United States Patent [19]
Kurtz et al.

[11] Patent Number: 5,261,897
[45] Date of Patent: Nov. 16, 1993

[54] PORTABLE SUCTION SYSTEM

[75] Inventors: Robert J. Kurtz, New York; Joseph LiCausi, Port Jefferson Station, both of N.Y.

[73] Assignee: BioResearch, Inc., Farmingdale, N.Y.

[21] Appl. No.: 621,882

[22] Filed: Dec. 4, 1990

[51] Int. Cl.⁵ .............................................. A61M 1/00
[52] U.S. Cl. ................................... 604/321; 604/317; 137/205; 137/528
[58] Field of Search ................. 137/846, 205, 528; 604/317–324

[56] References Cited

U.S. PATENT DOCUMENTS

| | | | |
|---|---|---|---|
| 3,898,701 | 8/1975 | LaRussa | 137/846 |
| 4,372,336 | 2/1983 | Cornell et al. | 604/318 |
| 4,605,400 | 8/1986 | Kurtz et al. | 604/319 |
| 4,619,647 | 10/1987 | Kurtz et al. | 604/320 |
| 4,650,477 | 3/1987 | Johnson | 604/320 |
| 4,675,011 | 6/1987 | Kurtz et al. | 604/319 |

Primary Examiner—Randall L. Green
Assistant Examiner—Rob Clarke
Attorney, Agent, or Firm—Larson & Taylor

[57] ABSTRACT

A portable suction system is provided for use with collection chambers for pleural drainage devices and for autotransfusion systems. The portable suction system comprises a small container having an inlet port for connection with a collection chamber or autotransfusion bag and an outlet port for connection with a suction source. The container includes a one-way valve system to prevent air from passing into the collection chamber or auto-transfusion bag and further includes a suction regulator and indicator to visually indicate the suction level.

4 Claims, 3 Drawing Sheets

PORTABLE SUCTION SYSTEM

FIELD OF THE INVENTION

The present invention relates to a portable reusable suction system to be used with collection chambers of drainage devices and autotransfusion bags.

BACKGROUND OF THE INVENTION

Integral pleural drainage devices have been in common use since 1967 and have now totally replaced the three bottle system which was used prior to the development of the integral devices as disclosed in U.S. Pat. No. 3,363,626 issued Jan. 16, 1968. Such devices included a collection chamber for collecting fluid from the pleural cavity, a water seal to prevent air from entering the pleural cavity and a suction regulating system. The use of the water seal necessitates the provision of a column of water of at least 30 centimeters in height in order to prevent loss of the water seal and air entering the pleural cavity. It is, of course, quite possible that even higher degrees of negativity may exist in the pleural cavity under certain circumstances and in order to prevent loss of the water seal and to prevent air entering the pleural cavity, a float valve has been provided in the water seal chamber as shown in U.S. Pat. No. 3,683,913 issued Aug. 15, 1972.

More recently drainage devices have become more complex and include diagnostic tools which were not available to the physician previously. For example, in U.S. Pat. No. 4,605,400 issued Aug. 12, 1986 there is disclosed a bellows for indicating the respiration of a patient and in addition this patent discloses a bubble chamber for indicating the passage of air bubbles from the patient's pleural cavity to the suction source. Obviously, the addition of the diagnostic tools to the drainage device has substantially increased the cost of the disposable integral pleural drainage device.

In U.S. Pat. No. 4,883,476 issued Nov. 28, 1989, there is disclosed a drainage device in which the collection chamber which is disposable may be separated from a nondisposable section which contains all the diagnostic tools as well as the suction regulator and seal chamber. However, a need has arisen for a relatively small portable suction regulator and seal which can be used with either a separable disposable drainage device or with an autotransfusion bag.

SUMMARY OF THE INVENTION

According to the present invention there is provided a small portable reusable container which incorporates within it a suction regulator, one-way valve to prevent air from entering the pleural cavity, a bellows to indicate the respiration of the patient, a bubble chamber and a suction indicator. All of these diagnostic elements are incorporated in a container which is approximately 3 inches square and one inch in depth. The container is provided with an inlet which may be connected with a separate collection chamber or with an autotransfusion bag and an outlet is provided on the container for connection with a suction source.

By using a one-way valve submerged in liquid as a seal to prevent air from passing into the pleural cavity it is unnecessary to provide a column 30 centimeters in height as is the case with conventional water seals. While there are disclosures in the prior art of one-way valves used in place of the conventional water seal as shown, for example, in U.S. Pat. No. 4,605,400, these valves have not always functioned properly in operation. With the types of one-way valves used in the present invention wherein the valve is submerged in liquid, it has been found that the valves operate without malfunction.

The suction regulating system utilized in the present invention comprises a single valve having an elongated tapered external surface cooperating with an elongated tapered valve seat which provides a means for accurate regulation of the degree of suction maintained within the container. While there are disclosed in the prior art, such as, for example, U.S. Pat. No. 4,605,400 one-way valves which are used to regulate the suction level within a drainage device, such one-way valves have not proven effective in regulating the degree of negativity with the accuracy of the present invention.

An object of the present invention is to provide a small portable reusable suction system to be interposed between a collection chamber of a drainage device or an autotransfusion bag and a source of suction.

A further object of the present invention is to provide a small container having an inlet and outlet with a suction regulator, one-way seal, bubble chamber, respiration indicator and suction level indicator.

Other objects and many of the attendant advantages of the present invention will become more readily apparent upon consideration of the following detailed specification when considered in connection with the accompanying drawings wherein:

DETAILED DESCRIPTION OF THE INVENTION

Figure 1:
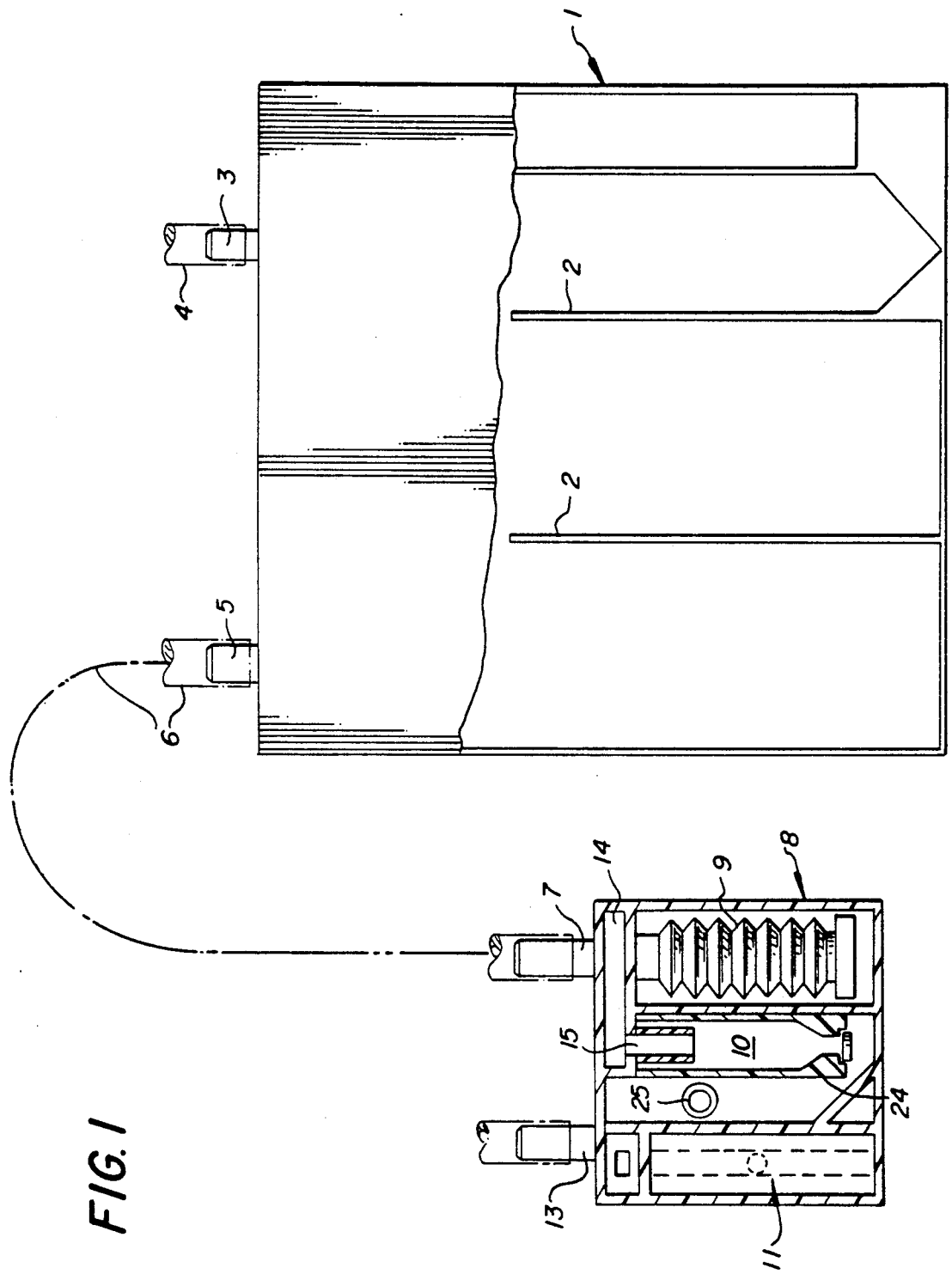
FIG. 1 is a side elevation of a drainage device connected to a portable suction system according to the present invention.

Referring now more specifically to the drawings wherein like numerals indicate like parts throughout the several views, there is shown at 1 in FIG. 1 a collection chamber for a pleural drainage device. Collection chamber 1 is provided with a plurality of partitions 2 so that when the first chamber is filled with fluid from the patient's pleural cavity, the liquid will overflow the first chamber and pass into the second chamber. An inlet 3 is provided which interconnects with a thoracotomy tube 4 which has the distal end thereof in communication with the pleural cavity of a patient. The outlet 5 of the collection chamber 1 has a connecting tube 6 which has the distal end thereof press fit over the inlet 7 of the container 8 which includes the suction control regulator, one-way valve seal, respiratory indicator and suction level indicator which serves to maintain the appropriate degree of negativity within the collection chamber 1 and within the pleural cavity of the patient.

Figure 5:
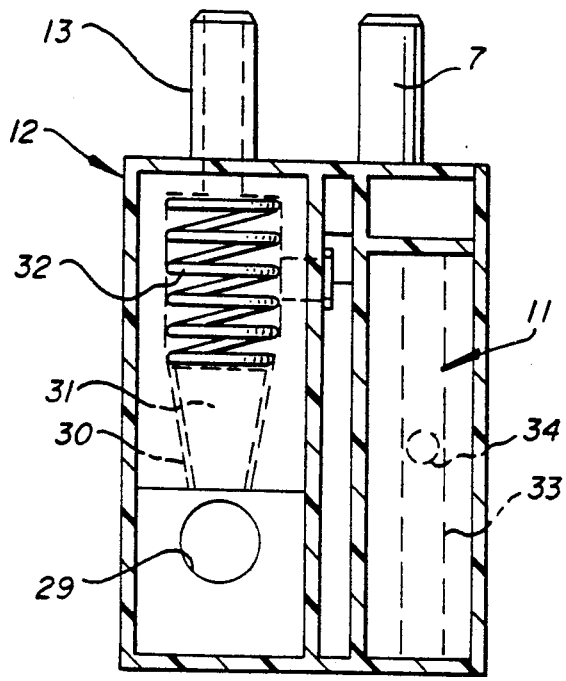
FIG. 5 is a vertical sectional view along the lines 5—5 of FIG. 2.
Figure 6:
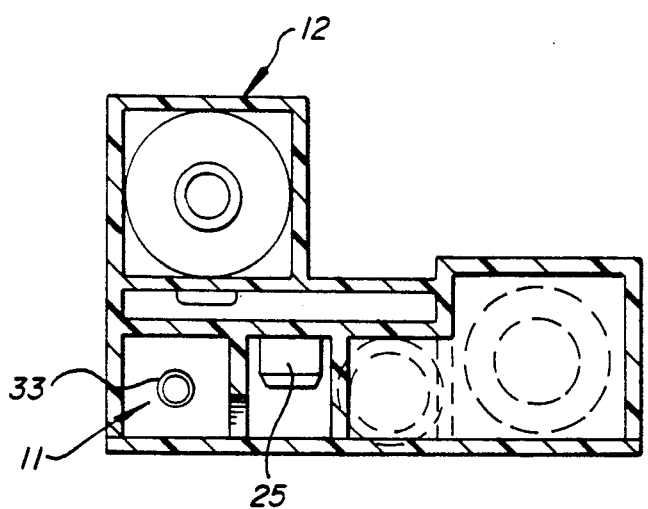
FIG. 6 is a cross sectional view along the line 6—6 of FIG. 2

As shown in FIG. 1 there is disposed within the container a bellows 9 which permits the physician to observe the respiratory movements of the patient's lungs. There is also provided a one-way valve chamber 10 which serves to prevent air from passing into the pleural cavity of the patient and a suction indicator 11 which visually indicates the suction level existing within the container. In addition, there is provided a suction regulator 12 as seen in FIGS. 5 to 7 which suction regulator has an outlet 13 which is connected to a suction source.

Figure 2:
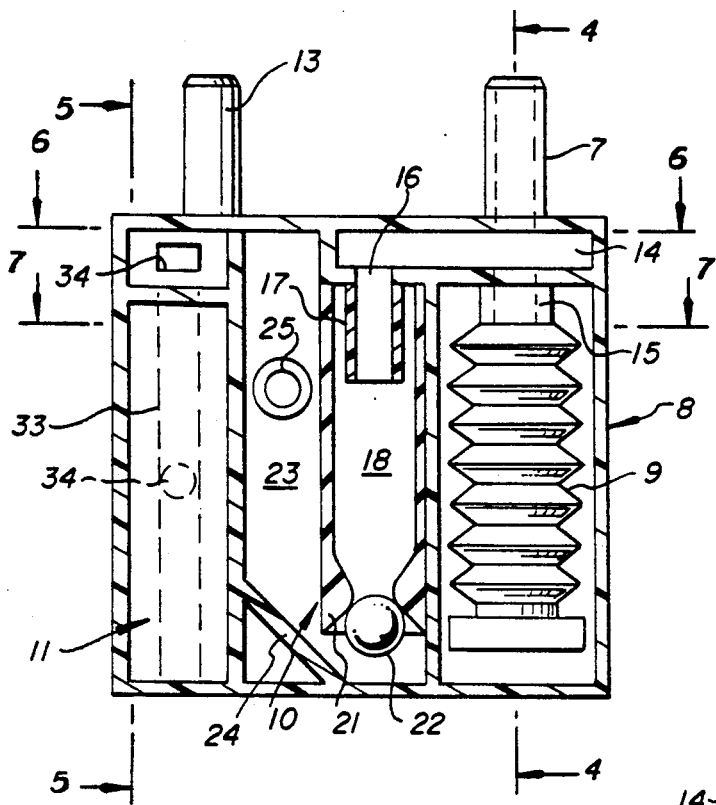
FIG. 2 is a vertical sectional view illustrating a portable suction system with a modified type of one-way valve.

As shown in FIGS. 1 and 2, there is provided a passageway 14 which is in communication with the inlet opening 7. There is provided an opening 15 in the bottom wall of passageway 14 which is in communication with the interior of bellows 9. There is further provided at the opposite end of passageway 14 an orifice 16 with a tube 17 projecting downwardly from the opening 16 into a vertically extending chamber forming the first passageway of the one-way valve chamber 10. The lower end of the passageway 18 has a valve seat 19 formed thereon. The valve seat 19 as shown in FIG. 1 has a circular recess to receive a disk valve 20 therein. In the FIG. 2 embodiment, the valve seat 21 is shaped to receive a ball valve 22. Immediately adjacent the first vertical passageway 18 there is provided a second vertical passageway 23 and it can be seen that the lower ends of the passageways 18 and 23 are in fluid communication. As shown in FIGS. 1 and 2, there is provided a partition 24 which reduces the volume of the common passageway between passageways 18 and 23 to prevent the disk valve 20 or ball valve 22 from becoming displaced into the second passageway 23.

Figure 4:
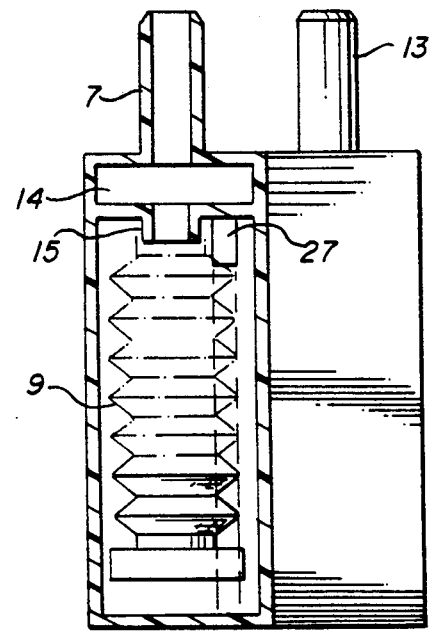
FIG. 4 is a sectional view along the lines 4—4 of FIG. 2.
Figure 7:
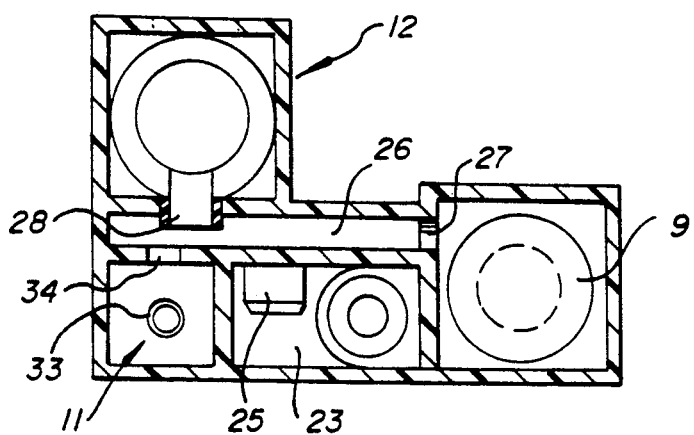
FIG. 7 is a cross sectional view along the line 7—7 of FIG. 2.

As shown in FIGS. 1 to 3, 6 and 7 there is provided a tubular passageway 25 extending from the second vertical passageway 23 in the one-way valve chamber 10. Passageway 25 is in communication with an elongated air flow chamber 26 (FIG. 7). There is provided an opening 27 in on end of the chamber 26 which communicates with the outer surface of the bellows 9 as seen in FIGS. 4 and 7. The chamber 6 is also provided with a passageway 28 (FIG. 7) in communication with the suction regulator 12.

The suction regulator 12 (FIG. 5) comprises a lower end portion provided with at least one opening to atmosphere 29. It may be desirable to provide a number of openings to atmosphere on various walls of the suction regulator chamber 12 in the event that one opening becomes inadvertently blocked. The internal wall of the suction regulator chamber 12 is tapered at the lower end, the tapered portion of the wall extending for a length of at least a ¼ of an inch and more preferably between ⅜ to ⅝ of an inch in length. An opening is provided in the bottom wall of the suction regulator chamber 12 and a valve 31 having a tapered wall is spring pressed by spring 32 to close the opening in the bottom wall of the suction regulator. The spring 32 is adjusted so as to apply sufficient resistance to valve 31 to maintain the degree of negativity within the container 8 at −20 cm of water when the outlet 13 is connected to a source of suction. It can be seen that the suction level is maintained within the chamber of the suction regulator 12 above the valve 31 and within the passageway 26 which communicates with the external surface of the bellows 8 and the same degree of negativity is delivered through the tubular passageway 25 through the one-way valve chamber 10 and into the collection chamber 1 and in the pleural cavity of the patient. It has been found that by utilizing the elongated tapered surfaces as disclosed herein, a more accurate control of the degree of negativity within the device is obtained.

Figure 3:
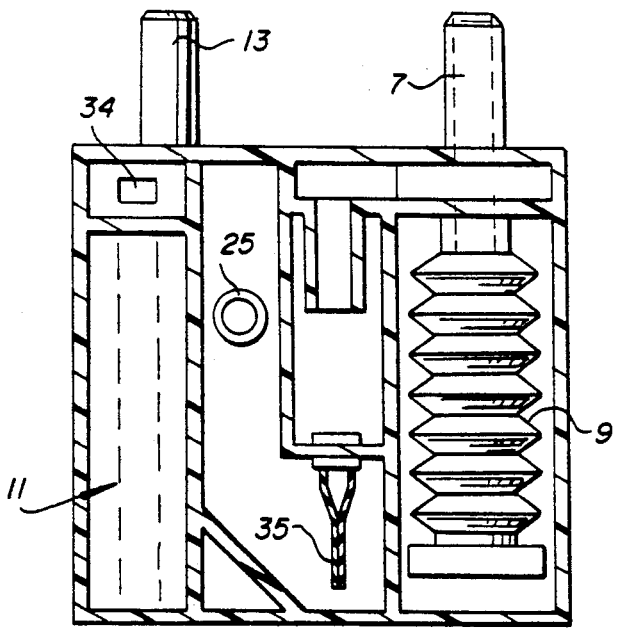
FIG. 3 is a vertical sectional view similar to FIG. 2 illustrating another embodiment of a one-way valve.

The suction indicator chamber 11, as seen in FIGS. 2, 3 and 5 comprises a tube 33 having the lower end thereof open to atmosphere with the upper end of the tube in communication with a chamber having a opening 34 in communication with the chamber 26. A ball 34 is disposed within the tube 33. In operation when suction is applied to the device, atmospheric air will pass up the tube 11 and through the opening 34 into chamber 26. This air flow will cause the ball 34 to rise within the tube and the transparent face on the container 8 may be provided with indicia to indicate the level of suction within the device as determined by the position of the ball 34 in tube 33.

In FIG. 3 there is shown a duck bill valve 35 which may be used in place of the ball valve 22 or disk valve 20. The duck bill valve functions in a manner similar to a Hemlich valve. A flexible tube has an end portion with a slit therein between a pair of flexible flaps which normally urge the flaps together so as to maintain the valve closed. When sufficient pressure is exerted from the interior of the valve, the flaps will separate to open the valve. The duck bill valve disclosed herein may be made from 630 or 830 RTV rubber with a length of approximately 1 ¼ inch and an internal diameter of 0.452 inch. The cracking pressure for this type of valve is equivalent to about 1.5 cm of water. The distal end of the duck bill valve may be submerged in 5 cm of water so that an internal pressure equivalent to 2 cm of water is required to open the duck bill valve.

In use, glycerin or other suitable liquid is provided in the one-way valve chamber 10, generally liquid is filled to approximately 2 cm in height within the second vertical passageway 23 when the disk valve 20 or ball valve 22 are used. The disk valve 20 and ball valve 22 float and when there is at least 2 cm of fluid within the chamber 23 the valves will be forced up in firm engagement with the valve seats. Similarly, the duck bill valve 35 will remain completely closed by the pressure of the liquid on the outer surfaces of the flat valve. The one-way valves provided by the disk valve, ball valve and duck bill valve prevent air from entering the first vertical passageway 18 and thus perform the function of the water seal in prior art systems. The suction regulator maintains the degree of negativity within the collection chamber or autotransfusion bag at the desired degree of negativity. The suction indicator indicates the level of suction within the device and, when the device is used with a pleural drainage collection chamber, the bellows 9 will move upwardly and downwardly in response to the respiratory efforts of the patient. In addition, when a patient has an air leak and the degree of negativity within the patient's pleural cavity is less than the predetermined desired negativity level by more then 2 cm of water, the air will be drawn through the one-way seal and the glycerin within the seal chamber will indicate the passage of bubbles therethrough.

Obviously man modifications and variations of the present invention are possible in light of the above teachings. What is claimed as new and desired to be secured by Letters Patent is:

We claim:

1. A portable suction system comprising, in combination, a container, inlet and outlet openings in the top wall of the container, the inlet opening adapted to be connected to an outlet opening of a collection chamber completely independent of said container, the outlet opening in said container being adapted to be connected to a source of suction, first and second vertically extending passageways in said container, said first passageway having a valve seat therein, the lower ends of said passageways being interconnected by a common passageway, liquid filling the common passageway at the lower ends of the first and second passageways, one way valve means disposed at the lower end of said first passageway, said one way valve means floating on the liquid forming the water seal and engaging said valve seat to close the first passageway when the suction level in the first passageway is equal to or greater than the suction level in the second passageway and said one way valve means opening to permit air to flow through the liquid from the first passageway to the second passageway when the suction level in the second passageway is greater than the suction level in the firs passageway, and means to prevent said one way valve means from moving into said second passageway.

2. A portable suction system according to claim 1 wherein the height of said passageways is substantially less than 30 centimeters.

3. A portable suction system according to claim 1 and further including a bellows in said container, a passageway connecting the interior of said bellows with the container inlet, the exterior of said bellows being subjected to the pressure at the container outlet.

4. A portable suction system according to claim 1 wherein said container further includes suction regulating means disposed in communication with said second passageway and said outlet.

* * * * *